United States Patent [19]
Ferdman et al.

[11] Patent Number: 5,951,531
[45] Date of Patent: Sep. 14, 1999

[54] APPARATUS AND METHOD FOR APPLYING A PARTICULATE HEMOSTATIC AGENT TO LIVING TISSUE

[75] Inventors: Ariel G. Ferdman, Rio Piedras, Puerto Rico; Vladimir J. Pinsky, Brighton, Mass.

[73] Assignee: Medchem Products, Inc., Woburn, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/532,604
[22] PCT Filed: Apr. 15, 1994
[86] PCT No.: PCT/US94/04193
§ 371 Date: Jan. 25, 1996
§ 102(e) Date: Jan. 25, 1996
[87] PCT Pub. No.: WO94/23788
PCT Pub. Date: Oct. 27, 1994

Related U.S. Application Data

[63] Continuation-in-part of application No. 08/049,818, Apr. 20, 1993, abandoned.

[51] Int. Cl.$^6$ .................................................. A61M 35/00
[52] U.S. Cl. ............................ 604/290; 604/24; 604/70; 604/82; 606/213; 606/214
[58] Field of Search .................................. 604/24, 23, 61, 604/49, 51, 52, 53, 58, 59, 60, 70, 82–84, 191, 140, 131, 146, 57, 147, 289, 290, 68, 71, 73, 500, 506–508; 222/195, 635, 372, 373, 376; 602/50–52, 56, 48; 606/213–215, 228, 229; 239/143, 325, 311, 336, 338, 346, 364–369, 373, 406, 407; 128/200.15, 200.21, 200.22, 200.23

[56] References Cited

U.S. PATENT DOCUMENTS

| | | |
|---|---|---|
| H257 | 4/1987 | Barditch et al. . |
| 881,238 | 3/1908 | Hasbrouck ................................ 604/58 |
| 3,742,955 | 7/1973 | Battista et al. . |
| 4,204,645 | 5/1980 | Hopp . |
| 4,578,067 | 3/1986 | Cruz, Jr. .................................. 604/368 |
| 4,631,055 | 12/1986 | Redl et al. ................................ 604/82 |
| 4,655,211 | 4/1987 | Sakamoto et al. . |
| 4,846,405 | 7/1989 | Zimmermann . |

(List continued on next page.)

FOREIGN PATENT DOCUMENTS

| | | |
|---|---|---|
| 3024749 | 2/1982 | Germany . |
| 1 254 534 | 11/1971 | United Kingdom . |

OTHER PUBLICATIONS

Sinyakevich, V. I., et al.., "Press Working Surfaces Lubrication Plant—Has Compressed Air Operated Control Valve Measuring and Injecting Controlled Amounts of Lubricant" (From *Derwent Publication, Ltd.,* London, GB, Week 8340, Abstract of Soviet Union, Inventor's Certification No. 978999, dated Dec. 7, 1982).

*Primary Examiner*—Ronald K. Stright, Jr.
*Attorney, Agent, or Firm*—Wolf, Greenfield & Sacks, P.C.

[57] ABSTRACT

An apparatus and method for applying a particulate hemostatic agent to living tissue are disclosed. The apparatus includes a particulate hemostatic agent source (22) and a continuous gas source (14). A continuous gas stream from the continuous gas source is turbulently combined with the particulate hemostatic agent within the hemostatic agent source from a finely dispersed fluid stream of the particulate hemostatic agent in the continuous gas stream. An outlet conduit (34) extends from where the gas and particulate hemostatic agent are combined through an outlet (36) of the conduit, whereby the fluid stream is conducted through the outlet conduit and is discharged from the outlet conduit onto proximate living tissue, thereby applying the particulate hemostatic agent o the living tissue.

16 Claims, 2 Drawing Sheets

U.S. PATENT DOCUMENTS

| | | | |
|---|---|---|---|
| 4,872,450 | 10/1989 | Austad . | |
| 4,902,281 | 2/1990 | Avoy | 604/191 |
| 4,946,870 | 8/1990 | Partain, III et al. . | |
| 5,147,292 | 9/1992 | Kullas et al. | 604/34 |
| 5,219,328 | 6/1993 | Morse et al. | 604/49 |
| 5,226,567 | 7/1993 | Sansalone | 222/195 |
| 5,226,877 | 7/1993 | Epstein | 604/35 |
| 5,273,531 | 12/1993 | Knoepfler | 604/58 |
| 5,429,278 | 7/1995 | Sansalone | 222/195 |
| 5,445,612 | 8/1995 | Terakura et al. | 604/24 |
| 5,469,994 | 11/1995 | Reh et al. | 222/195 |
| 5,470,311 | 11/1995 | Setterstrom et al. | 604/24 |
| 5,538,162 | 7/1996 | Reh et al. | 222/195 |

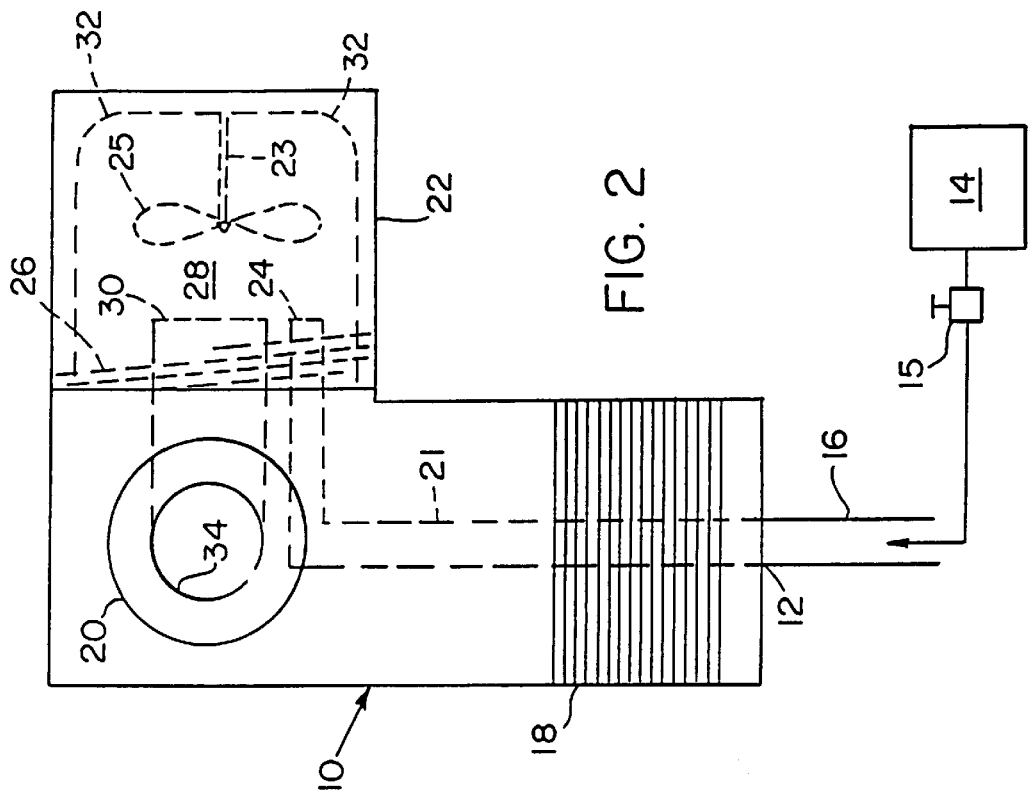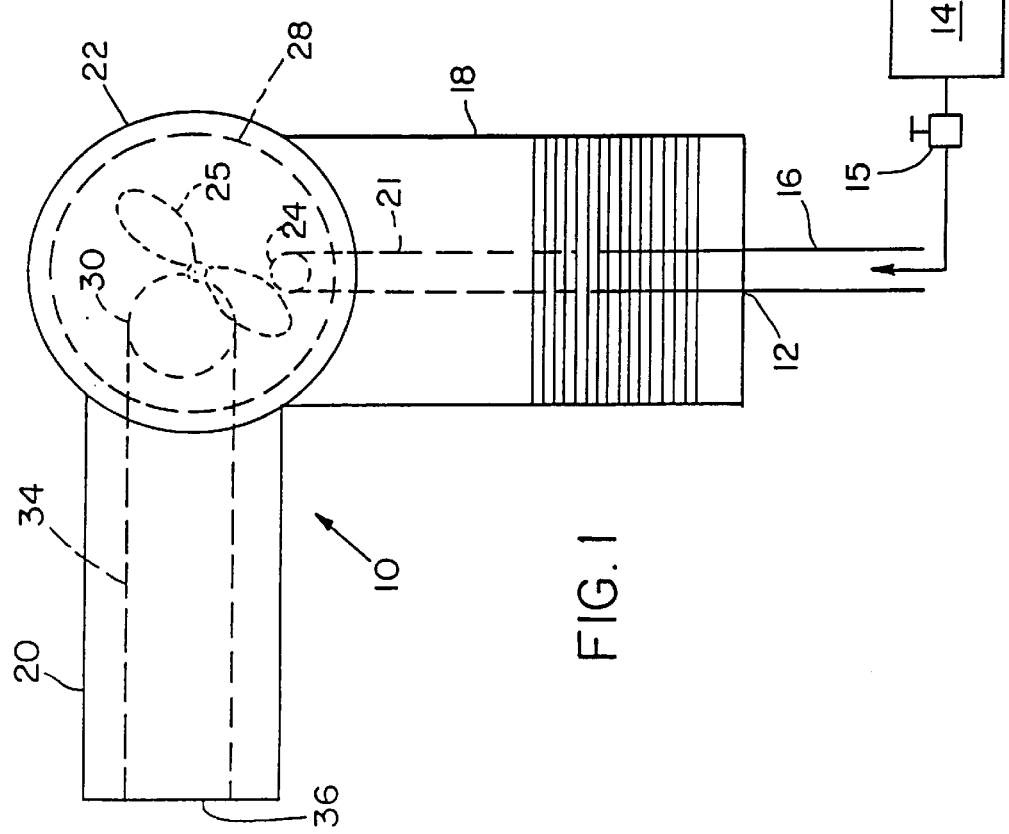

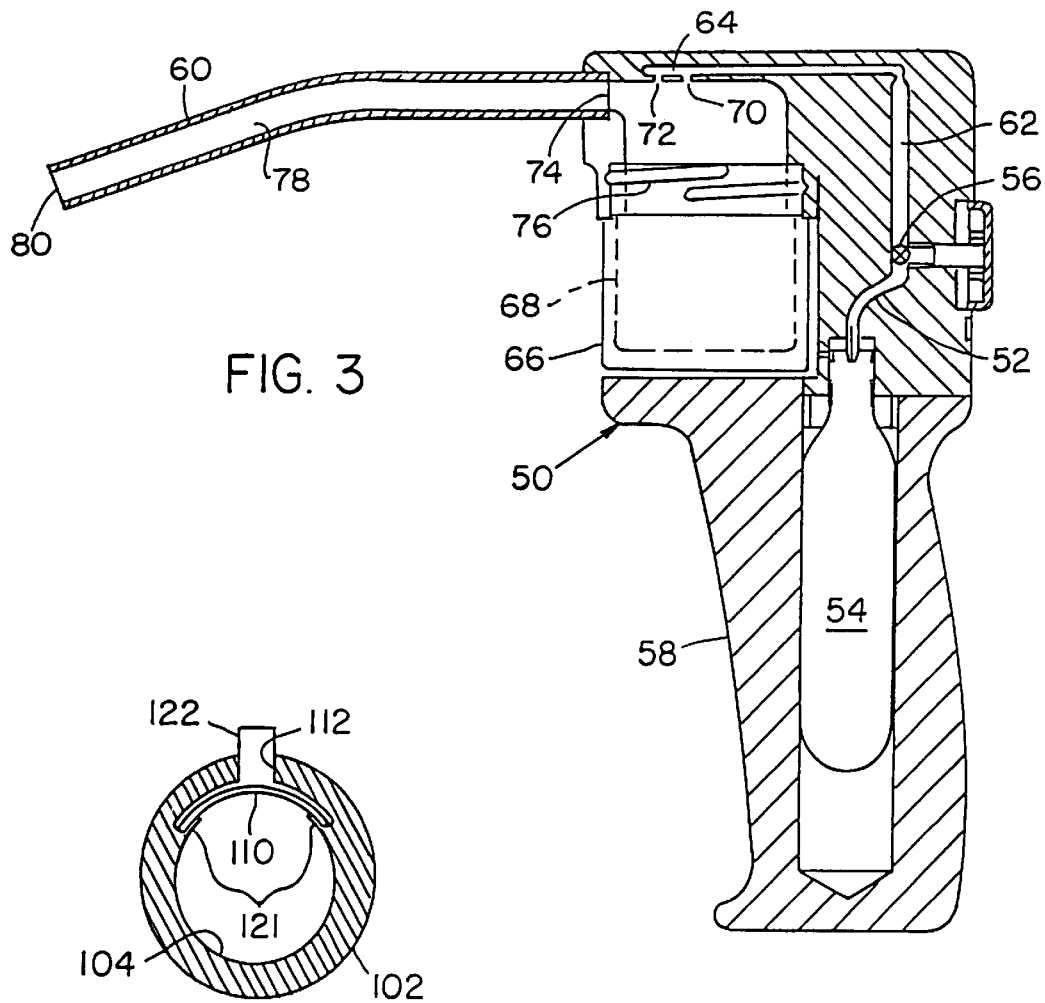
FIG. 3
FIG. 5
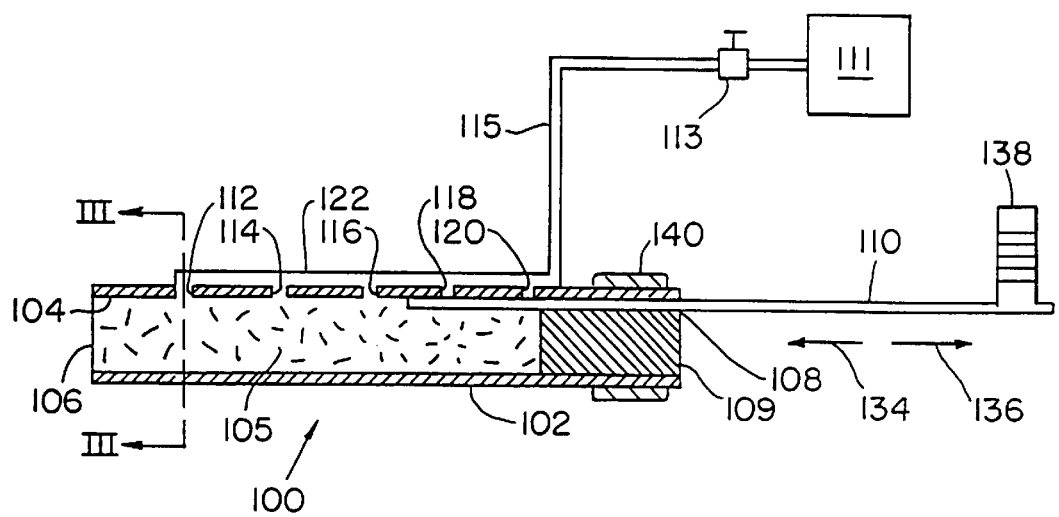
FIG. 4

APPARATUS AND METHOD FOR APPLYING A PARTICULATE HEMOSTATIC AGENT TO LIVING TISSUE

RELATED APPLICATIONS

This is a U.S. National Phase application of PCT/US94/04193, filed Apr. 15, 1994, which is a CIP of U.S. Ser. No. 08/049,818, filed Apr. 20, 1993 now abandoned.

BACKGROUND OF THE INVENTION

After tissue has been wounded or cut, the opening must be surgically closed to stop bleeding and enable healing of the tissue. In cases of severe wound and skin grafting, an insufficient amount of tissue can exist around the sides of the wound or surgical incision to allow the sides to be pulled together. Similarly, when diseased or blemished tissue is removed by surgery, insufficient tissue may be left around the perimeter of the removed tissue. These procedures are invasive and have substantial risks of complications, including that of infection.

One attempt to stem blood logs and to facilitate wound closure is application of a hemostatic agent, such as collagen, to the wound to form a wound dressing. The hemostatic agent, on contact with blood or other body fluids, adheres to the tissue and stems bleeding, However, hemostatic agents are extremely hydrophilic. Upon contact with moisture from the wound or the atmosphere, the fibrillar hemostats have a tendency to clump and adhere tenaciously to any object. These objects include instruments, gloves, non-bleeding tissues and other surfaces in addition to the intended open wound or surgical incision. This clumping and adhesion takes application of the hemostatic agent to the wound difficult. Conventional apparatus intended to suspend particulates in a gas, such as are taught in U.S. Pat. No. 4,204,645, issued on May 27, 1986 to Hepp, and U.S. Statutory Invention Registration H257, are typically not suitable for application of hemostatic agents because the agents tend to agglomerate and consequently plug the apparatus.

SUMMARY OF THE INVENTION

The present invention relates to an apparatus and method for applying a particulate hemostatic agent to living tissue.

The apparatus includes a particulate hemostatic agent source, a continuous gas source and means for combining a turbulent continuous gas stream from the gas source with the particulate hemostatic agent within the hemostat agent source to form a finely dispersed fluid stream of the particulate hemostatic agent in the gas. The apparatus further includes an outlet conduit extending from means for combining the gas and particulate hemostatic agent through an outlet of the conduit, whereby the fluid stream is conducted through the outlet conduit and is discharged from the outlet conduit onto proximate living tissue, thereby applying the particulate hemostatic agent to the living tissue.

The method includes the steps of combining a turbulent continuous gas stream with the particulate hemostatic agent to form a finely dispersed fluid stream of the particulate hemostatic agent in the gas. The fluid stream is directed through an outlet conduit, whereby the fluid stream is conducted through the outlet conduit and onto proximate living tissue, thereby applying the particulate hemostatic agent to the living tissue.

This invention has many advantages which include an apparatus that allows accurate placement by a surgeon of the particulate hemostatic agent onto a bleeding site. The apparatus is easy to hold and to use, and it allows the surgeon to view the placement of the particulate hemostatic agent on the tissue. By forming a finely dispersed fluid stream of the hemostatic agent in a turbulent continuous gas stream, the apparatus minimizes the problem of sticking or clumping before reaching the targeted wound or surgical incision and allows for control of the amount of particulate hemostatic agent applied.

BRIEF DESCRIPTION OF THE DRAWINGS

FIG. 1 is an orthogonal projection side view of one embodiment of the apparatus of the present invention.

FIG. 2 is an orthogonal projection end view of the embodiment shown in FIG. 1.

FIG. 3 is a second embodiment of the apparatus of the present invention.

FIG. 4 is an orthogonal projection side view of a third embodiment of the apparatus of the present invention.

FIG. 5 is an orthogonal projection end view of the third embodiment shown in FIG. 3 taken along line III—III.

DETAILED DESCRIPTION OF THE INVENTION

The features and other details of the method and apparatus of the invention will now be more particularly described with reference to the accompanying drawings and pointed out in the claims. The same numeral present in different figures represents the same item. It will be understood that the particular embodiments of the invention are shown by way of illustration and not as limitations of the invention. The principle features of this invention can be employed in various embodiments without departing from the scope of the invention.

One embodiment of the invention, as shown in FIG. 1, a side view, and in FIG. 2, an end view, is spray device 10, which can be a hand held device. As can be seen in FIG. 1, spray device 10 has gas inlet 12 for receiving a continuous gas stream from continuous gas source 14 through gas tube 16. A continuous gas stream is considered one that can be maintained without interruption or cessation for an extended period of time, although the flow rates can be varied over the period of time. Gas tube 16 is flexible and sufficiently resilient to direct a continuous gas stream at a velocity of between about 20 and 200 cm/sec. The flow of continuous gas stream can be controlled by valve 15. In one embodiment, valve 15 is activated by a floor mounted pedal switch which can be operated by a surgeon using his foot.

A suitable gas is one that can form a fluid stream of particulate hemostatic agent by combination with a particulate hemostatic agent. In one embodiment, the gas is substantially inert in the presence of the particulate hemostatic agent and living tissue. Example of such gases include air, nitrogen, helium, argon, carbon dioxide, etc., or a combination thereof. These gases should be sterile because they come in contact with the open wound or surgical incision in the living tissue. Further, the gas has a low-humidity content because suitable particulate hemostatic agents generally have a tendency to clump when exposed to moisture. Typically, the gas has a relative humidity of less than about thirty percent.

Spray device 10 has handle 18 and nozzle 20. Handle 18 can be sized so as to be easily held with one hand. Handle 18 can be made of metal or other material which would readily allow a secure grip by the surgeon or operator of the device. Gas inlet passage 21 is disposed within handle 18 for receiving the continuous gas stream from gas tube 16 and directing the gas through particulate hemostatic agent source gas inlet 24 to particulate hemostatic agent source 22 to form a fluid stream of the particulate hemostatic agent in the gas.

A wide variety of particulate hemostatic agents can be used with this invention. For example, the particulate hemostatic agent can include cellular fibers which act as chemical agents to stop bleeding of living tissue. Examples of a suitable particulate hemostatic agent include collagen, non-soluble polysaccharide, cellulose and dried gelatin. Collagen can be obtained from many mammalian sources, such as from the hides of cows, pigs, sheep, goats, etc., and can be denatured. The particulate hemostatic agent can be in the form of fibers, powder, flakes, particles, milled fibrillar particles, etc. which can readily form of fluid stream in a continuous gas stream for transporting and dispersing the hemostatic agent. Generally, the density of the hemostatic agent is in the range of between about one and four pounds/ft$^3$ (0.016–0.064 g/cm$^3$). A particularly suitable collagen hemostatic agent is commercially available as Avitene® fibrillar hemostatic agent, from MedChem Products, Inc., Woburn, Mass. Another hemostatic agent is a gelatin powder commercially available under the trademark of Gelfoam® from Upjohn Corporation.

As can be seen in FIG. 2, particulate hemostatic agent source 22 is attached to spray device 10 by suitable means, such as screw threads 26 or by other means, such as a clamp, etc. Particulate hemostatic agent source 22 has source chamber 28 for containing the hemostatic agent. In one embodiment, the amount of particulate hemostatic agent in particulate hemostatic agent source 22 is about one gram. The interior of source chamber 28 is shaped to allow the entering gas to mix sufficiently with the particulate hemostatic agent to break up and disperse any agglomeration of hemostatic agent and to form a finely dispersed fluid suspension within chamber 28. The suspension is directed from particulate hemostatic agent source 22 through particulate hemostatic agent source outlet 30 to form a turbulent fluid stream of particulate hemostatic agent. In one embodiment, source chamber 28 has curved corners 32 to direct the gas within source chamber 28, thereby assisting in directing the continuous gas stream to combine with the particulate hemostatic agent and form a fluid stream therewith.

Turbine means 25 which is held in place by support 23 can be placed within particulate hemostatic agent source 22 to allow the formed fluid stream to be more finely dispersed. Turbine means 25 is propelled by the continuous gas stream as it is directed through particulate hemostatic agent source 22. Rotation of turbine means 25 substantially prevents agglomeration of particulate hemostatic agent in source 22 while the gas stream is being directed through source 22.

Returning to FIG. 1, nozzle 20 has interior conduit 34, which extends from particulate hemostatic agent source 22 to conduit outlet 36. Preferably, interior conduit 34 has a substantially constant internal diameter along the length of nozzle 20 through outlet 36. Also, conduit outlet 36 has the same shape and size of the cross section of interior conduit 34. In one embodiment, nozzle 20 is about twenty centimeters long, and conduit 34 and conduit outlet 36 both have a diameter of about 1.25 centimeters.

The continuous gas stream is directed from continuous gas source 14 through gas tube 16 to gas inlet 12 of gas inlet passage 21 of spray device 10. In one embodiment, a gas, such as dry nitrogen gas, is directed at a velocity of between about 20 and 200 cm/sec. The continuous gas stream is directed from gas inlet passage 21 through particulate hemostatic agent source inlet 24 to particulate hemostatic agent source 22.

Particulate hemostatic agent source 22 has particles of hemostatic agent which are sufficiently small to allow the directed gas to form a fluid stream. The particulate hemostatic agent and the continuous gas stream are mixed sufficiently within particulate hemostatic agent source 22' to form a fluid stream of particulate hemostatic agent in the gas. The fluid stream is directed from particulate hemostatic agent outlet 30 through interior conduit 34. The particulate hemostatic agent is then directed from conduit outlet 36 onto a proximate wound or incision. Conduit outlet 36 is positioned proximate to the surface of the tissue so that the fluid stream can be spread over the wound or incision, thereby forming a layer of particulate hemostatic agent.

Another embodiment of the invention, as shown in FIG. 3, is a spraying device 50, which can be a hand held device and is portable. As can be seen in FIG. 3, spraying device 50 has gas inlet tube 52 for receiving a continuous gas stream from gas source 54. The flow of continuous gas stream can be controlled by valve 56. In one embodiment, valve 56 is activated by a hand-pushed button.

Spraying device 50 has handle 58 and nozzle 60. Gas inlet passage 62 is disposed within spraying device 50 for receiving the continuous gas stream from gas tube 52 and directing the gas through particulate hemostatic agent source gas inlet 64 to particulate hemostatic agent source 66 which has particulate hemostatic agent chamber 68 for containing the hemostatic agent to form a fluid stream of the particulate hemostatic agent in the gas. Particulate hemostatic agent source gas inlet 64 has inlet conduits 70,72. First inlet conduit 70 allows a jet of gas to enter particulate hemostatic agent chamber 68 and mix with the particulate hemostatic agent to provide a continuous supply of suspended hemostatic agent by causing turbulent agitation of the agent inside particulate hemostatic agent chamber 68 thereby forming a dispersed fluid suspension of particulates within chamber 68. In a preferred embodiment, first inlet conduit 70 directs the jet of gas turbulently into particulate hemostatic agent chamber 68. Second inlet conduit 72 is sufficiently proximate to particulate hemostatic chamber outlet 74 to allow the gas entering particulate hemostatic agent chamber 68 to break up and disperse throughout chamber 68 any agglomeration of particulate hemostatic agent that would otherwise block particulate hemostatic chamber outlet 74 while the gas stream is directed through particulate hemostatic agent source 66, thereby allowing the particulate hemostatic agent to be discharged through particulate hemostatic chamber outlet 74 as a finely dispersed fluid stream. Particulate hemostatic agent chamber gas inlet 64 is not necessarily limited to the exemplified two conduits. For instance, gas inlet 64 can have a plurality of conduits distributed through the top of particulate hemostatic agent chamber 68 with at least one conduit proximate to particulate hemostatic chamber outlet 74.

Particulate hemostatic agent chamber 68 is attached to spraying device 50 by suitable means, such as threads 76. The interior of particulate hemostatic agent chamber 68 is shaped to allow the entering gas to mix sufficiently with the particulate hemostatic agent to form a fluid stream of particulate hemostatic agent source 66 through particulate hemostatic chamber outlet 74, thereby forming a fluid stream of particulate hemostatic agent.

Nozzle 60 has interior conduit 78, which extends from particulate hemostatic agent source 66 to conduit outlet 80.

Conduit outlet 80 has the same shape and size of the cross section of interior conduit 78. In one embodiment, nozzle 60 is about eight centimeters long and interior conduit 78 and conduit outlet 80 both have a diameter of about 0.5 centimeters.

Another embodiment of the invention, as shown in FIG. 4, a side view, and in FIG. 5, which is an end view taken along line III—III of FIG. 4, is spray apparatus 100. As can be seen in FIG. 4, spray apparatus 100 includes cylinder 102. Cylinder 102 has interior passage 104 which has a substantially constant internal diameter the length of cylinder 102 through outlet 106. In other words, the diameter of outlet 106 is about the same as that of interior passage 104. Cylinder 102 is suitable for holding particulate hemostatic agent 105 therein.

Opening 108 at end 109 is configured for receiving slidable valve gate 110. Valve gate 110 is sufficiently sized and shaped to slide along the interior of cylinder 102 through second opening 108 while not allowing a significant amount of gas to pass between cylinder 102 and valve gate 110. As shown in FIG. 5, valve gate 110 is held in place by protrusions 121 within interior passage 104 of cylinder 102.

Returning to FIG. 4, inlets 112, 114, 116, 118, 120 can be of constant or varying cross-sectional area. Alternatively, the inlet can be a slot which extends along the conduit. Inlets 112, 114, 116, 118, 120 have a sufficient diameter to allow a gas to pass through the inlets and enter cylinder 102.

The flow of gas from continuous gas source 111 through tube 115 to gas distributor 122 is controlled by valve 113 which can be activated by a floor mounted pedal switch. Gas distributor 122 is placed substantially along the length of cylinder 102 and has a plurality of outlets that allows the gas stream to form a plurality of streams through gas inlets 112, 114, 116, 118, 120.

Spraying apparatus 100 is operated by sliding valve gate 110 in direction 136 along the interior of cylinder 102 to thereby successively open gas inlets 112, 114, 116, 118, 120. To close gas inlets 112, 114, 116, 118, 120, valve gate 110 is closed by sliding in direction 134. For example, as gas inlet 112 is opened, gas is directed through the inlet into cylinder 102, thereby displacing particulate hemostatic agent in cylinder 102 between the opening and outlet 106. The displaced particulated hemostatic agent is consequentially directed out of cylinder 102 through outlet 106 and onto proximate tissue. When at least a substantial portion of the hemostatic agent has been discharged from between gas inlet 112 and outlet 106, slide valve gate 106 is further retracted to open gas inlet 114. Hemostatic agent in cylinder 102 between gas inlets 112 and 114 is thereby displaced. The hemostatic agent is consequently directed by the gas stream out of cylinder 102 through outlet 106 onto the proximate tissue. As each successive gas inlet is opened by sliding movement of valve gate 110, the particulate hemostatic agent is controllably discharged from apparatus 100, thereby forming a layer of the particulate hemostatic agent on a proximate wound or incision, thereby stemming bleeding and facilitating tissue closure.

Spraying apparatus 100 is composed of materials that can be easily cleaned and sterilized, such as stainless steel. The components of spraying apparatus 100 are easily disassembled to remove any particulate hemostatic agent deposited within the interior of spraying apparatus.

The amount of particulate hemostatic agent directed onto a wound or incision is dependent on the concentration of particulate hemostatic agent in the fluid stream. For example, the concentration can be about thirty grams per liter. The gas velocity can be in the range of between about twenty and two hundred centimeters per second.

Equivalents

Those skilled in the art will recognize, or be able to ascertain using no more than routine experimentation, many equivalents to the specific embodiments of the invention described specifically herein. Such equivalents are intended to be encompassed in the scope of the claims.

We claim:

1. A method for applying a solid particulate hemostatic agent to living tissue, comprising the steps of:

a) combining a turbulent continuous gas stream with a solid particulate hemostatic agent to form a finely dispersed fluid stream of said solid particulate hemostatic agent in said gas; and b) directing the finely dispersed fluid stream through an outlet conduit having a substantially constant internal diameter, whereby said fluid stream is conducted through the outlet conduit and onto proximate living tissue, thereby applying the solid particulate hemostatic agent to the living tissue.

2. The method of claim 1 wherein the solid particulate hemostatic agent is collagen.

3. The method of claim 2 wherein the collagen is substantially denatured.

4. The method of claim 3 wherein the collagen is in the form of flakes.

5. The method of claim 3 wherein the collagen is in the form of a powder.

6. The method of claim 2 wherein the collagen is in the form of milled fibrillar particles.

7. The method of claim 6 wherein the gas is selected from the group consisting of air, nitrogen, carbon dioxide, helium and argon.

8. The method of claim 1 wherein the solid particulate hemostatic agent is cellulose.

9. The method of claim 1 wherein the solid particulate hemostatic agent is a non-soluble polysaccharide.

10. A method for applying a solid particulate hemostatic agent to a living tissue, comprising:

combining a turbulent continuous gas stream with a solid particulate hemostatic agent to form a finely dispersed fluid stream of the solid particulate hemostatic agent in the gas; and directing the finely dispersed fluid stream through an outlet conduit, whereby the fluid stream is conducted through the outlet conduit and on to proximate living tissue, thereby applying the solid particulate hemostatic agent to the living tissue.

11. The method of claim 10, wherein the solid particulate hemostatic agent is selected from the group consisting of cellulose, a non-stable polysaccharide, and collagen.

12. The method of claim 11, wherein the solid particulate hemostatic agent is collagen and wherein the collagen is substantially denatured.

13. The method of claim 11, wherein the solid particulate hemostatic agent is collagen and the collagen is in the form of flakes.

14. The method of claim 11, wherein the solid particulate hemostatic agent is collagen and wherein the collagen is in the form of a powder.

15. The method of claim 11, wherein the solid particulate hemostatic agent is collagen and wherein the collagen is in the form of milled fibrillar particles.

16. The method of claim 10, wherein the gas is selected from the group consisting of air, nitrogen, carbon dioxide, helium, and argon.

\* \* \* \* \*